United States Patent
Rhoads et al.

(10) Patent No.: US 10,948,489 B2
(45) Date of Patent: Mar. 16, 2021

(54) METHOD OF DETECTING A SUBSTANCE

(71) Applicant: Purdue Research Foundation, West Lafayette, IN (US)

(72) Inventors: Jeffrey Frederick Rhoads, Lafayette, IN (US); Eric A. Nauman, West Lafayette, IN (US); Mackenzie Tweardy, West Lafayette, IN (US); Michael Wadas, West Lafayette, IN (US); Allison Kelly Murray, Canton, IN (US); George Tsu-Chih Chiu, West Lafayette, IN (US); Nikhil Bajaj, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 65 days.

(21) Appl. No.: 16/040,504

(22) Filed: Jul. 19, 2018

(65) Prior Publication Data

US 2019/0025296 A1    Jan. 24, 2019

Related U.S. Application Data

(60) Provisional application No. 62/534,374, filed on Jul. 19, 2017.

(51) Int. Cl.
  *G01N 33/543*   (2006.01)
  *G01N 33/547*   (2006.01)
  (Continued)

(52) U.S. Cl.
  CPC ....... *G01N 33/54393* (2013.01); *C07K 16/18* (2013.01); *G01N 33/547* (2013.01);
  (Continued)

(58) Field of Classification Search
  None
  See application file for complete search history.

(56) References Cited

U.S. PATENT DOCUMENTS

| 4,236,893 A | * | 12/1980 | Rice | G01N 33/54373 310/312 |
| 2005/0250222 A1 | * | 11/2005 | Kurosawa | G01N 33/5308 436/527 |
| 2008/0204043 A1 | * | 8/2008 | Wang | B82Y 30/00 324/633 |

OTHER PUBLICATIONS

Park et al. Stabilizing Effect of Artificial Stabilizers for Binding Activity of QCM Immunosensors, IEEE Transactions on Ultrasonics, Ferroelectrics and Frequency Control, vol. 50, No. 10, pp. 1234-1235. (Year: 2003).*

* cited by examiner

*Primary Examiner* — Melanie Brown
(74) *Attorney, Agent, or Firm* — Purdue Research Foundation (57) ABSTRACT

A method of detecting a substance, wherein the method includes functionalizing a plurality of sensors, wherein the functionalizing the plurality of sensors comprises depositing a first material using a piezoelectrically actuated pipette system, wherein the first material includes a polymer, a receptor, and a solvent, wherein the solvent comprises dimethylformamide. The method further includes evaporating a solution of the first material wherein a residue after the evaporation comprises a functionalized chemical. Additionally, the method includes introducing a control material to a first set of sensors of the plurality of sensors using the piezoelectrically actuated pipette system. Further, the method includes introducing a test material to a second set of sensors of the plurality of sensors using the piezoelectrically actuated pipette system, wherein the test material comprises an analyte. Moreover the method includes deter- (Continued)

(Left) Close up view of a 16 MHz plate-style resonator prior to functionalization. (Right) The same resonator after functionalization.

mining a difference between a first resonant frequency shift in the first set of sensors of the plurality of sensors and a second resonant frequency shift in the second set of sensors of the plurality of sensors.

20 Claims, 5 Drawing Sheets

(51) Int. Cl.
    *C07K 16/18*     (2006.01)
    *C08L 25/06*     (2006.01)

(52) U.S. Cl.
    CPC ........ *G01N 33/54373* (2013.01); *C08L 25/06* (2013.01); *G01N 2333/4727* (2013.01)

(Left) Close up view of a 16 MHz plate-style resonator prior to functionalization. (Right) The same resonator after functionalization.

Figure 2

Piezoelectrically actuated pipette system. A 200 μm diameter nozzle was used to deposit 5.0 nL of anti-s100β and polystyrene in DMF onto the surface of each sensor.

Figure 3

Frequency response of a 16 MHz resonator driven by a 200 mV amplitude signal both before and after exposure to a solution of PBS containing s100β. The shift of the resonant frequency is caused by the adsorption of s100β onto the sensor's surface.

METHOD OF DETECTING A SUBSTANCE

TECHNICAL FIELD

The present application relates to a method of detecting a substance by determining resonant frequency shift.

BACKGROUND

Piezoelectrically transduced resonant microsystems have emerged as a promising detection tool. Their high sensitivities make them excellent candidates for the mass-based detection of substances such as biomarkers, metals, biological compounds etc. Detection of some of these substances can help diagnose certain diseases and medical conditions, or even be helpful in other industries.

SUMMARY

The mechanism for detection relies on the relationship between the mass and resonant frequency of a lumped-mass system. The relationship is denoted by $\omega^2 = K/m$, where $\omega$ is the resonant frequency. K is the effective spring constant and m is the effect mass associated with the vibration mode of interest. The mass added to the resonator as a result of the adsorption of a substance (such as a biomarker), $\Delta m$, is then approximated as: $\Delta m = K((1/\omega_1^2) - (1/\omega_2^2))$, wherein $\omega_1^2$ and $\omega_1^2$ are the resonant frequencies of the resonator before and after the adsorption of the substance, respectively. This relationship implies that a change in the mass on the surface of a resonator caused by the binding of the substance will induce a resonant frequency shift. Furthermore, the sensitivity of the resonator increases as the resonant frequency increases, making high-frequency resonators excellent candidates for biomarker detection. If the surface of such a resonator can be functionalized to allow for the specific adsorption of a biomarker, metal, or of a biological compound of interest, the binding of that substance will cause a change in mass that is detectable via frequency response analysis.

One aspect of the present disclosure includes a method of detecting a substance, wherein the method includes functionalizing a plurality of sensors, wherein the functionalizing the plurality of sensors comprises depositing a first material using a piezoelectrically actuated pipette system, wherein the first material includes a polymer, a receptor, and a solvent, wherein the solvent comprises dimethylformamide. The method further includes evaporating a solution of the first material, wherein a residue after the evaporation comprises a functionalized chemical. Additionally, the method includes introducing a control material to a first set of sensors of the plurality of sensors using the piezoelectrically actuated pipette system. Further, the method includes introducing a test material to a second set of sensors of the plurality of sensors using the piezoelectrically actuated pipette system, wherein the test material comprises an analyte. Moreover the method includes determining a difference between a first resonant frequency shift in the first set of sensors of the plurality of sensors and a second resonant frequency shift in the second set of sensors of the plurality of sensors.

BRIEF DESCRIPTION OF THE DRAWINGS

One or more embodiments are illustrated by way of example, and not by limitation, in the figures of the accompanying drawings, wherein elements having the same reference numeral designations represent like elements throughout. It is emphasized that, in accordance with standard practice in the industry, various features may not be drawn to scale and are used for illustration purposes only. In fact, the dimensions of the various features in the drawings may be arbitrarily increased or reduced for clarity of discussion.

DETAILED DESCRIPTION

In the following description, some aspects will be described in terms that would ordinarily be implemented as software programs. Those skilled in the art will readily recognize that the equivalent of such software can also be constructed in hardware, firmware, or micro-code. Because data-manipulation algorithms and systems are well known, the present description will be directed in particular to algorithms and systems forming part of, or cooperating more directly with, systems and methods described herein. Other aspects of such algorithms and systems, and hardware or software for producing and otherwise processing the signals involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Various embodiments of the present disclosure relate to methods of detecting a substance. In one or more embodiments, the present methodology can be used for a wide variety of analytes such as such as biomarkers, metals, biological compounds, etc. In at least one embodiment, the versatility of the present process allows for a wide range of polymers and their associated solvents to be used for the purposes of functionalizing the sensors with receptors. A non-exhaustive list of receptor-analyte combination, along with polymer-solvent combination is disclosed herein as well. Based on the explanation in the Summary section, differences in resonances between when the potential analyte is adsorbed by the receptor, and the control material are calculated, thereby rendering differences in mass. These differences in mass help identify if there is a presence of an analyte of interest.

Figure 1:
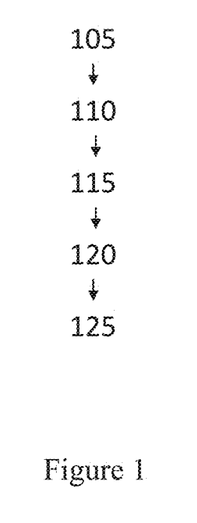
FIG. 1 illustrates a method of detecting a substance in accordance with one or more embodiments.

FIG. 1 is a flow chart of a method of detecting a substance in accordance with one or more embodiments. Method 100 begins with operation 105 which includes functionalizing a plurality of sensors, wherein the functionalizing the plurality of sensors comprises depositing a first material using a piezoelectrically actuated pipette system, wherein the first material comprises a polymer, a receptor, and a solvent. The deposition techniques in operation 105 include inkjet printing, evaporation based deposition, or spin coat deposition. Method 100 then continues with operation 110 which includes evaporating a solution from the first material, wherein a residue after the evaporation comprises a functionalized chemical.

Method 100 continues with operation 115 which includes introducing a control material to a first set of sensors of the plurality of sensors using the piezoelectrically actuated pipette system. Method 100 further continues with operation 120 which includes introducing a test material to a second set of sensors of the plurality of sensors using the piezoelectrically actuated pipette system, wherein the test material comprises an analyte. Method 100 additionally continues with operation 125 which includes determining a difference between a first resonant frequency shift in the first set of sensors of the plurality of sensors and a second resonant frequency shift in the second set of sensors of the plurality of sensors.

In at least one embodiment as it relates to method 100, the polymer includes polystyrene, the receptor includes anti-s100β, the solvent includes dimethylformamide, and the analyte includes s100β. In at least one embodiment, the depositing the first material includes depositing an amount of the suspension or solution of polymer (e.g. polystyrene) and receptor (e.g. anti-s100β) in solvent (e.g. dimethylformamide) on each sensor of the plurality of sensors. In some embodiments, the amount ranges from approximately $10^{-12}$ liters to approximately 10 milliliters. In some embodiments, the amount is approximately 5 nano-liters.

In one or more embodiments, a concentration of polymer (e.g. polystyrene) ranges from approximately 0.01 milligrams per milliliter to approximately 10 milligrams per milliliter, and a concentration of receptor (e.g. anti-s100β) ranges from approximately 0.01 milligrams per milliliter to approximately 10 milligrams per milliliter. In some embodiments, a concentration of polymer (e.g. polystyrene) is approximately 1.333 mg/mL and a concentration of receptor (e.g. anti-s100β) is approximately 0.106 mg/mL. In some embodiments, the solution of the first material includes dimethylformamide, or another chemical, depending on the type of solvent used for the polymer.

After the evaporation step (i.e. operation 110), the residue is a coating of a polymer (e.g. polystyrene) and a receptor (e.g. anti-s100β). Because this coating is functionalized, it is now able to adsorb specific substances (such as s100β).

Operation 115 additionally includes the control material, where the control material includes phosphate buffered saline, an inert substance, a protein that is neither the receptor or the analyte, or water. The amount of control material to each sensor ranges from approximately $10^{-12}$ liters to approximately 10 milliliters. In some embodiments, the introducing the control material includes introducing 5.0 nL of the control material to each sensor of the first set of sensors of the plurality of sensors.

Operation 120 additionally includes introducing an amount of the test material to each sensor of the second set of sensors of the plurality of sensors. In some embodiments, the amount ranges from approximately $10^{-12}$ liters to approximately 10 milliliters. In at least one embodiment, the analyte of operation 120 includes s100β. In one or more embodiments, a concentration of analytes (e.g. s100β) ranges from approximately $10^{-12}$ grams per milliliter to approximately 10 milligrams per milliliter. In some embodiments, a concentration of analytes (e.g. s100β) is approximately 19.6 µg/mL. In at least one embodiment, the introducing the test material includes introducing 5.0 nL of the test material to each sensor of the second set of sensors of the plurality of sensors.

Operation 125 additionally includes determining the resonant frequency shift using a lock-in amplifier, in at least one embodiment. In one or more embodiments, each sensors of the plurality of sensors in method 100 is a quartz crystal resonator. MEMs resonator, or a nano resonator. In some embodiments, each sensor of the plurality of sensors has a dimension of 3.2 mm by 2.5 mm. In some embodiments, each sensor of the plurality of sensors has a dimension of X mm by Y mm, where X ranges from $10^6$ m to 10 mm and Y ranges from $10^6$ m to 10 mm.

The polymer used in the above process includes polycarbonate, Poly(methyl methacrylate), Acrylonitrile butadiene styrene, a synthetic polymer, Polybenzimidazole, Polycarbonate, Polyether sulfone, polyoxymethylene, polyetherether ketone, polyetherimide, polyethylene, polypropylene, or Poly(lactic acid).

One of ordinary skill in the art would recognize that operations are added or removed from method 100, in one or more embodiments. One of ordinary skill in the art would also recognize that an order of operations in method 100 is able to be changed, in some embodiments. A non-exhaustive, but exemplary list of polymers and their associated solvents which can be used in method 100 is illustrated in Table 1. Additionally, a non-exhaustive, but exemplary list of receptors and their associated analytes which can be used in method 100 is illustrated in Table 2.

TABLE 1

| Polymer | Solvent |
| --- | --- |
| Acrylonitrile butadiene styrene (ABS) plastic | DMF + 0.1% LiBr |
| Acrylonitrile butadiene styrene (ABS) plastic | THF |
| Acrylonitrile styrene acrylate (ASA) plastic | THF |
| Adipate polyesters | THF |
| Alkanes | TCB |
| Alkyd resin | THF |
| Alkyl glycerides | THF |
| Alkyl glycerides | THF |
| Alkyl glycerides | THF |
| Alkylketene dimer (AKD) | THF |
| ASA Plastic | THF |
| Asphalt | o-Xylene |
| Asphalt | THF |
| Bisphenol-A, quantification | THF |
| Bitumin | o-Xylene |
| Bitumin | THF |
| Butyl rubber | Hexane |

TABLE 1-continued

| | |
|---|---|
| Carbomer (PAA) | Water + 0.2M $NaNO_3$ + 0.01M $NaH_2PO_4$ adjusted to pH 7 |
| Carboxymethyl cellulose (CMC) | Water + 0.5M $Na_2SO_4$ |
| Carboxymethyl cellulose (CMC) | Water + 0.2M $NaNO_3$ + 0.01M $NaH_2PO_4$ at pH 7 |
| Cellulose | DMAc + 0.5% LiBr |
| Cellulose | DMSO + 0.1% LiBr |
| Cellulose acetate | DMAc + 0.5% LiCl |
| Chitosan | Water + 0.5M $NaNO_3$ + 0.01M $NaH_2PO_4$ at pH 2 |
| Comb polymer, Polyacrylate | THF |
| Comb polymer, rubber, synthetic | THF |
| Corn flour | DMSO + 0.1% LiBr |
| Dextran | Water + 0.2M $NaH_2PO_4$ + 0.2M NaCl at pH 7 |
| Dextran | Water + 0.2M $NaNO_3$ + 0.01M $NaH_2PO_4$ |
| Diglycidyl ether bisphenol-A (DGEBA) | THF |
| Emeraldine | NMP + 0.1% LiBr |
| Epoxy prepreg resin | THF |
| Epoxy resin | DMF + 0.1% LiBr |
| Epoxy resin oligomers | THF |
| Epoxy resin oligomers | THF |
| Epoxy resin oligomers | THF |
| Epoxy resin, commercial | THF |
| Epoxy resin, high MW | THF |
| Ethylene vinyl acetate (EVA) | TCB + 0.015% BHT |
| Fatty acid methyl esters (FAME) | THF |
| Fatty acid methyl esters (FAME) | THF |
| Flavonoids | THF |
| Fluoroelastomer | THF |
| Gelatin | Water + 0.2M $NaNO_3$ + 0.01M $NaH_2PO_4$ at pH 7 |
| Glycerides | THF |
| Glycerides | THF |
| Glycerides | THF |
| Gum arabic | Water + 0.01M $NaH_2PO_4$ + 0.2M $NaNO_3$ at pH 7 |
| Hyaluronic acid | Water + 0.2M $NaNO_3$ + 0.01M $NaH_2PO_4$ at pH 7 |
| Hydrocarbons, linear | TCB |
| Hydrocarbons, linear | TCB |
| Hydrocarbons, long chain | TCB |
| Hydrocarbons, long chain | TCB |
| Hydrocarbons, short chain | TCB |
| Hydroxyethyl cellulose | DMF + 0.1% LiBr |
| Hydroxyethyl cellulose | Water + 0.05M $NaH_2PO_4$ + 0.25M NaCl at pH 7 |
| Hydroxyethyl cellulose, Modified | Water + 0.05M $NaH_2PO_4$ + 0.25M NaCl at pH 7 |
| Isocyanate prepolymers | Dichloromethane |
| Isocyanate prepolymers | THF |
| Isocyanate resin | THF |
| Lignin | DMF + 0.1% LiBr |
| Lignin | DMSO + 0.1% LiBr |
| Maltodextrins, in starch | Water + 0.2M $NaNO_3$ + 0.01M $NaH_2PO_4$, adjusted to pH 7 |
| Melamine resin | DMAC + 1% LiBr |
| Melamine resin | DMSO + 0.1% LiBr |
| Melamine-formaldehyde resin | DMF |
| Methyl cellulose | Water + 0.05M $NaH_2PO_4$ + 0.25M NaCl at pH 7 |
| Natural rubber, vulcanized | Toluene |
| Novalac | DMF |
| Novalac | THF |
| Novalac resin | DMF + 0.1% LiBr |
| Novalac resin | DMSO + 0.1% LiBr |
| Nylon | HFIP + 20 mM NaTFA |
| Nylon | m-Cresol |
| Nylon 6, low MW | THF |
| Odorants, essential oils, acid esters | THF |
| Oil, lubricant, certified 3100 MW | THF |
| Oil, lubricant, petroleum jelly | THF |
| Oligopin | THF |
| Oligosaccharides | NMP |
| Oligosaccharides, xylose | Water |
| Paint, resin, commercial | THF |
| Pectin | Water + 0.2M $NaNO_3$ + 0.01M $NaH_2PO_4$, adjusted to pH 7 |

TABLE 1-continued

| | |
|---|---|
| Pectin | Water + 0.2M $NaNO_3$ + 0.01M $NaH_2PO_4$ at pH 7 |
| Petroleum jelly | THF |
| Phenol distillate residue | Acetone |
| Phenol-formaldehyde resin | DMF + 0.1% LiBr |
| Phenol-formaldehyde resin | THF |
| Phthalates, dialkyl, Plasticizer | THF |
| Polacrylate, comb | THF |
| Poloxamer | DMF + 0.1% LiBr |
| Poly(2-vinyl pyridine) | Water + 0.2M $NaNO_3$ + 0.01M $NaH_2PO_4$ at pH 7 |
| Poly(2-vinyl pyridine) | Water + 0.8M $NaNO_3$ + 0.01M $NaH_2PO_4$ at pH 3 |
| Poly(4-bromostyrene) | THF |
| Poly(acrylates) | DMAc + 0.5% LiBr |
| Poly(acrylates) | DMF + 0.1% LiBr |
| Polyacrylonitrile (PAN) | DMF + 0.1% LiBr |
| Poly(aminostyrene - vinyl pyrrolidone) | Water + 0.2M $NaNO_3$ + 0.01M $NaH_2PO_4$, adjusted to pH 7 |
| poly(ester-imide) | THF |
| Poly(ethylene oxide), high MW | DMF + 0.1% LiBr |
| poly(ethylene-vinyl acetate) (PEVA) | TCB + 0.015% BHT |
| Poly(isobornyl methacrylate) (IBMA) | THF |
| poly(lactic-co-glycolic acid) (PLGA) | Chloroform |
| poly(lactic-co-glycolic acid) (PLGA) | THF |
| Poly(methyl vinyl ether-maleic acid) | Water + 0.2M $NaNO_3$ + 0.01M $NaH_2PO_4$, adjusted to pH 7 or pH 9 as appropriate |
| Poly(methyl vinyl ether-maleic acid) alkyl esters | Water + 0.2M $NaNO_3$ + 0.01M $NaH_2PO_4$, adjusted to pH 7 or pH 9, as appropriate |
| Poly(n-isopropylacrylamide) (PNIPAM) | THF + 5% TEA |
| Poly(styrene-isoprene) Block Copolymer | THF |
| Poly(styrene butadiene) Copolymer (SBR) | THF |
| Poly(vinyl chloride) (PVC) | THF |
| Poly(vinylidene fluoride) (PVDF) | DMSO |
| Polyacrylamide (PAM) | Water + 0.05M $Na_2SO_4$ at pH 3 |
| Polyacrylamide (PAM) | Water + 0.2M $NaNO_3$ + 0.01M $NaH_2PO_4$ at pH 7 |
| Polyacrylic acid (PAA) | Water + 0.2M $NaNO_3$ + 0.01M $NaH_2PO_4$, adjusted to pH 7 |
| Poly-alpha-olefin (PAO) | TCB + 0.015% BHT |
| Polyamide | HFIP + 20 mM NaTFA |
| Polyaniline | NMP + 0.1% LiBr |
| Polyanion, acrylic acid, sodium salt | Water + 0.2M $NaNO_3$ + 0.01M $NaH_2PO_4$, adjusted to pH 7 |
| Polyanion, polyacrylamide | Water + 0.05M $Na_2SO_4$ at pH 3 |
| Polyanion, polystyrene sulfonate | 80% [Water + 0.3M $NaNO_3$ + 0.01M $NaH_2PO_4$ at pH 9] + 20% Methanol |
| Polybromostyrene | THF |
| Polybutadiene | THF |
| Polybutylene Terephthalate (PBT) | HFIP + 20 mM NaTFA |
| Polybutyrate resin | THF |
| Polycaprolactam | HFIP + 20 mM NaTFA |
| Polycaprolactam | m-Cresol |
| Polycaprolactam, low MW | THF |
| Polycarbonate | Dichloromethane |
| Polycarbonate | THF |
| Polycation, poly(2-vinyl pyridine) | Water + 0.2M $NaNO_3$ + 0.01M $NaH_2PO_4$ at pH 7 |
| Polycation, poly(2-vinyl pyridine) | Water + 0.8M $NaNO_3$ + 0.01M $NaH_2PO_4$ at pH 3 |
| Polycation, poly(aminostyrene-vinyl pyrrolidone) | Water + 0.2M $NaNO_3$ + 0.01M $NaH_2PO_4$, adjusted to pH 7 PL aquagel-OH |
| Polycation, polyacrylamide | Water + 0.05M $Na_2SO_4$ at pH 3 |
| Polydimethyl siloxane (PDMS) | Toluene |
| Polyester | THF |
| Polyester, adipate resin | THF |
| Polyester, polyol resin | THF |
| Polyether ethyl ketone (PEEK) | 80% Chloroform + 20% Dichloroacetic acid |
| Polyether sulfone | DMF + 0.1% LiBr |
| Polyetherimide (PEI) | DMF + 0.1% LiBr |
| Polyethylene | TCB + 0.015% BHT |
| Polyethylene | TCB + 0.015% BHT |
| Polyethylene glycol (PEG) | DMF + 0.1% LiBr |
| Polyethylene glycol (PEG) | Water |
| Polyethylene glycol (PEG), branched | DMF + 0.1% LiBr |

TABLE 1-continued

| | |
|---|---|
| Polyethylene glycol, star | 70% [Water + 0.2M NaNO$_3$ + 0.01M NaH$_2$PO$_4$] + 30% methanol |
| Polyethylene terephthalate (PET) | 4-Chlorophenol |
| Polyethylene terephthalate (PET) | 2-Chlorophenol |
| Polyethylene, branched | TCB + 0.015% BHT |
| Polyethylene, LDPE | TCB + 0.015% BHT |
| Polyethylene, linear | TCB + 0.015% BHT |
| Polyethylene, linear, Metallocene (mPE) | TCB + 0.015% BHT |
| Polyhydroxyalkanoate (PHA) | Chloroform |
| Polyhydroxybutyrate (PHB) | Chloroform |
| Polyhydroxybutyrate (PHB) | Chloroform |
| Polyisocyanate | Dichloromethane |
| Polyisoprene | THF |
| Polyisoprene | Toluene |
| Polyisoprene, natural latex | Toluene |
| Polylactic acid (PLLA) | THF |
| Polymethacrylate, linear | THF |
| Polyol | THF |
| Polyol, prepolymer resin | THF |
| Polyphenol | THF |
| Polyphenylene sulphide (PPS) | 1-Chloronaphthalene |
| Polypropylene | TCB + 0.015% BHT |
| Polypropylene, commercial | TCB + 0.015% BHT |
| Polysaccharides | Water + 0.2M NaNO$_3$ + 0.01M NaH$_2$PO$_4$ |
| Polysaccharides, corn flour | DMSO + 0.1% LiBr |
| Polysaccharides, xylose oligomers | Water |
| Polysaccharides | NMP |
| Polysiloxane, commercial | THF |
| Polysiloxane, commercial | Toluene |
| Polyster resin | THF |
| Polystyrene | THF |
| Polystyrene sulfonate | 80% [Water + 0.3M NaNO$_3$ + 0.01M NaH$_2$PO$_4$ at pH 9] + 20% Methanol |
| Polystyrene, oligomers | THF |
| Polystyrene, oligomers | THF |
| Polystyrene, star branched | THF |
| Polysulfone | DMF + 0.1% LiBr |
| Polythiophene (PT) | TCB + 0.015% BHT |
| Polyurethane | THF |
| Polyurethane copolymer | DMAc + 0.02% LiBr |
| Polyurethane resin | Dichloromethane |
| Polyurethane resin | THF |
| Polyurethane, high MW | DMAc + 0.5% LiBr |
| Polyurethane, high MW | DMF + 0.1% LiBr |
| Polyvinyl acetate (PVAc) | THF |
| Polyvinyl alcohol (PVA) (PVOH) | Water + 0.2M NaNO$_3$ + 0.01M NaH$_2$PO$_4$ at pH 7 |
| Polyvinyl alcohol (PVA) (PVOH) | Water + 0.25M NaNO$_3$ + 0.01M NaH$_2$PO$_4$ at pH 7 |
| Polyvinyl alcohol (PVA) (PVOH), acetylated | THF |
| Polyvinyl alcohol (PVA) (PVOH), hydrophobic modified, surfactant | DMSO + 0.1% LiBr |
| Polyvinyl butyral (PVB) | THF |
| Polyvinylpyrrolidone (PVP) | DMAc + 0.5% LiCl |
| Polyvinylpyrrolidone (PVP) | DMF + 0.1% LiBr |
| Polyvinylpyrrolidone (PVP) | Water + 0.2M NaNO$_3$ + 0.01M NaH$_2$PO$_4$ at pH 3 |
| Proanthocyanidin | THF |
| Pullulan | Water + 0.2M NaNO$_3$ + 0.01M NaH$_2$PO$_4$ |
| PVC plastic | THF |
| Resol | DMF |
| Resol | THF |
| Silicone | Toluene |
| Silicone, commercial | THF |
| Silicone, commercial | Toluene |
| Sodium polyacrylate | Water + 0.2M NaNO$_3$ + 0.01M NaH$_2$PO$_4$, adjusted to pH 7 PL aquagel-OH |
| Starch | DMSO:DMAc (4:1) + 0.1% LiBr |
| Starch | NMP |
| Starch, corn | Water + 0.2M NaNO$_3$ + 0.01M NaH$_2$PO$_4$, adjusted to pH 7 PL aquagel-OH |
| Starch, potato | Water + 0.2M NaNO$_3$ + 0.01M NaH$_2$PO$_4$, adjusted to pH 7 PL aguagel-OH |

TABLE 1-continued

| | |
|---|---|
| Styrene butadiene rubber (SBR) | THF |
| Surfactant, enhanced oil recovery, polyacrylamide | Water + 0.05M $NaH_2SO_4$ at pH 3 |
| Surfactant, modified Polyvinyl alchol | DMSO + 0.1% LiBr |
| Surfactant, Poloxamer, Poly(PEG-PPG-PEG) | DMF + 0.1% LiBr |
| Tannins | THF |
| Tar, petroleum | o-Xylene |
| Tar, petroleum | THF |
| Tar, petroleum | THF |
| Tar, phenol distillate residues | Acetone |
| TINUVIN, light stabilizer, additive | THF |
| Triacetate, cellulose triacetate | DMAc + 0.5% LiCl |
| Ultem (PEI) | DMF + 0.1% LiBr |
| Varnish, soya oil, dried | THF |
| Vinyl, PVC plastic | THF |
| Vitaflavan | THF |
| Wax, beeswax | THF |
| Wax, microcrystalline, Hydrocarbon | THF |
| Wax, parrafin | TCB |
| Wax, parrafin | TCB |
| Xanthan gum | Water + 0.2M $NaNO_3$ + 0.01M $NaH_2PO_4$ at pH 7 |
| Xylooligosaccharide | Water |
| Polystyrene | DMF/THF (tetrahydrofuran) |
| Polyproplyene | TCB + 0.015% BHT |
| Polycarbonate | THF/Dichloromethane |
| Nylon | THF, m-Cresol, HFIP + 20 mM NaTFA |
| PLA (polylactic acid) | Chloroform |
| ABS (acrylonitrile butadiene styrene) | THF or DMF + 0.1% LiBr |

PLgel - A highly cross-linked polystyrene-divinylbenzene (PS-DVB) particle compatible with organic and many polar organic solvents. Brochure: 5990-7994EN
PolarGel - A proprietary particle chemistry designed for polar samples dissolved in polar organics and water/organic mixtures Brochure: 5990-7995EN
PL aquagel-OH- A hydrophilic particle chemistry compatible with water, high-salt buffers, and up to 50% methanol Brochure: 5990-7995EN
Chemical acronyms.
THF   Tetrahydrofuran
DMAc  Dimethylacetamide
NMP   N-methyl-2-pyrrolidone
HFIP  Hexafluorisopropanol
BHT   Butylated hydroxytoluene
DMF   Dimethylformamide
DMSO  Dimethylsulfoxide
TCB   1,2,4-Trichlorobenzene
NaTFA Sodium trifluoroacetate
TEA   Triethylamine
END OF TABLE 1

TABLE 2

| Analyte | Receptor/anti-body |
|---|---|
| Alpha-Synuclein | Alpha-Synuclein antibody |
| Aβ40 | Aβ40 antibody |
| Aβ42 | Aβ42 antibody |
| BDNF | BDNF antibody |
| c-MET | c-MET antibody |
| C-Peptide | C-Peptide antibody |
| CA 19-9 | CA 19-9 antibody |
| CA-125 | CA-125 antibody |
| Cathepsin S | Cathepsin S |
| CCL-11/Eotaxin Assay Kit | CCL-11/Eotaxin Assay Kit antibody |
| CEA | CEA antibody |
| CRP | CRP antibody |
| CXCL13 | CXCL13 antibody |
| Cytokine 3-Plex A TNFα, IL-6, IL-10 | Cytokine 3-Plex A TNFα, IL-6, IL-10 antibody |
| Cytokine 3-Plex B TNFα, IL-6, IL-17A | Cytokine 3-Plex B TNFα, IL-6, IL-17A antibody |
| G-CSF | G-CSF antibody |
| GFAP | GFAP antibody |
| GM-CSF | GM-CSF antibody |
| GM-CSF (mouse) | GM-CSF (mouse) antibody |
| HE4/WFDC2 | HE4/WFDC2 antibody |
| HIV p24 | HIV p24 antibody |
| IFN-γ | IFN-γ antibody |
| IFNα | IFNα antibody |
| IL-10 | IL-10 antibody |
| IL-12 p70 | IL-12 p70 antibody |
| IL-12p40/IL-23 | IL-12p40/IL-23 antibody |
| IL-13 | IL-13 antibody |
| IL-15 | IL-15 antibody |
| IL-17A | IL-17A antibody |
| IL-17A (mouse) | IL-17A (mouse) antibody |
| IL-17A/F (mouse) | IL-17A/F (mouse) antibody |
| IL-17C | IL-17C antibody |
| IL-17F | IL-17F antibody |
| IL-17F (mouse) | IL-17F (mouse) antibody |
| IL-18 | IL-18 antibody |
| IL-1α | IL-1α antibody |
| IL-1α (mouse) | IL-1α (mouse) antibody |
| IL-1β | IL-1β antibody |
| IL-1β (mouse) | IL-1β (mouse) antibody |
| IL-2 | IL-2 antibody |
| IL-22 (mouse) | IL-22 (mouse) antibody |
| IL-22 (Total) | IL-22 (Total) antibody |
| IL-23 | IL-23 antibody |
| IL-23 (mouse) | IL-23 (mouse) antibody |
| IL-28A | IL-28A antibody |

TABLE 2-continued

| Analyte | Receptor/anti-body |
|---|---|
| IL-3 | IL-3 antibody |
| IL-33 | IL-33 antibody |
| IL-36β | IL-36β antibody |
| IL-4 | IL-4 antibody |
| IL-6 | IL-6 antibody |
| IL-6 (mouse) | IL-6 (mouse) antibody |
| IL-8 | IL-8 antibody |
| IP-10 | IP-10 antibody |
| Leptin | Leptin antibody |
| LIF | LIF antibody |
| MCP-1 | MCP-1 antibody |
| MCP-3 | MCP-3 antibody |
| MIP-1β | MIP-1β antibody |
| NF-light ® | NF-light ® antibody |
| NSE | NSE antibody |
| NT-proBNP | NT-proBNP antibody |
| PD-1 | PD-1 antibody |
| PD-L1 | PD-L1 antibody |
| PlGF | PlGF antibody |
| pNF-Heavy | pNF-Heavy antibody |
| PSA | PSA antibody |
| Tau | Tau antibody |
| Tau (mouse) | Tau (mouse) antibody |
| TGFα | TGFα antibody |
| TGFβ | TGFβ antibody |
| TNFα | TNFα antibody |
| TNFα (mouse) | TNFα (mouse) antibody |
| TNPβ | TNPβ antibody |
| TRAIL | TRAIL antibody |
| Troponin-I | Troponin-I antibody |
| UCH-L1 | UCH-L1 antibody |
| VEGF | VEGF antibody |
| lead | EDTA (Ethylenediaminetetraacetic acid), DMSA (dimercaptosuccinic acid), or N-acetylcysteine |
| chromium | N-acetylcysteine |
| arsenic | Thiolates, amines, or dimercaprol |
| mercury | DMPS (sodium 2,3-dimercaptopropane 1-sulfonate) |

Example 1

In one or more embodiments, an analyte which can be identified using the above method is a biomarker by the name s100β, a protein closely associated with Traumatic Brain Injury (TBI). The concentrations of s100β in the cerebrospinal fluid of TBI victims immediately after injury typically increase from several ng/ml to several hundreds of ng/ml, making it a promising diagnostic biomarker for TBI.

The example starts off with using Plate-style, 16 MHz quartz crystal resonators (Kyocera Corp., CX3225) which act as the biomarker sensors. A single resonator measures 3.20 mm by 2.50 mm and can be seen in FIG. 2. Each sensor was integrated with a circuit that enables its frequency response characterization via an HF2LI Lock-In Amplifier (Zurich Instruments). The characterization was achieved with 1 Hz resolution over a 300 Hz frequency range containing the sensor's resonant frequency. From the frequency response, the peak frequency was taken to be the frequency that yields the highest magnitude output. Any shift in the peak frequency was assumed to be equivalent to a corresponding shift in the resonant frequency, an approximation supported by the high Q-factor of the resonators. A shift in the peak frequency therefore indicated an increase in mass on the surface of the resonator, thus enabling the detection of s100β.

Figure 2:
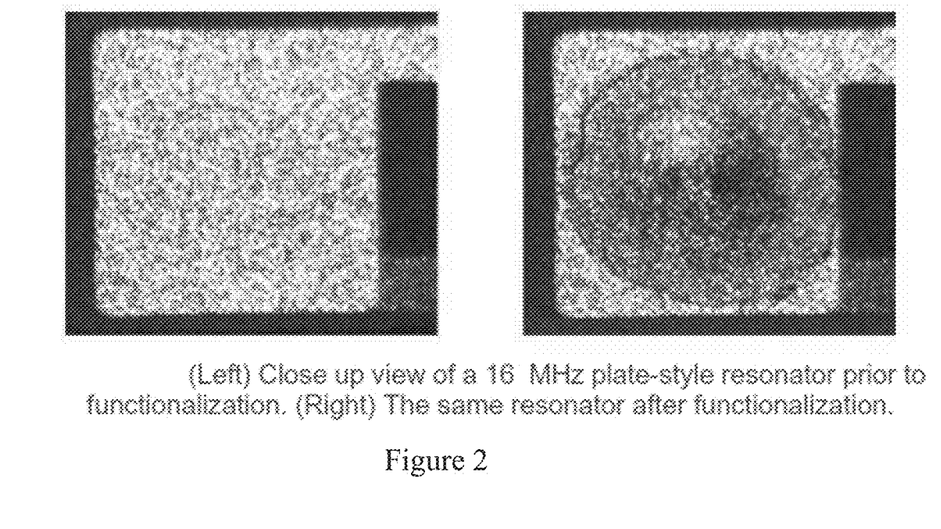
FIG. 2 illustrates a 16 MHz plate-style resonator prior to and after functionalization, in accordance with one or more embodiments.
Figure 3:
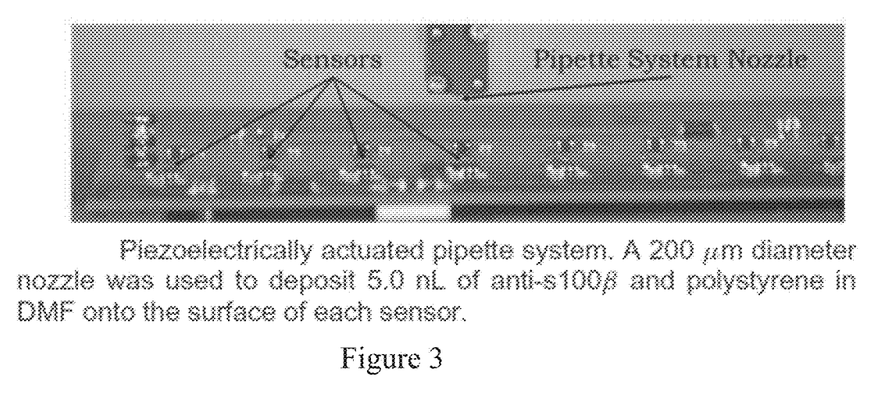
FIG. 3 illustrates a piezoelectrically actuated pipette system, in accordance with one or more embodiments.

To functionalize the sensors, polystyrene and anti-s100β (Abcam, 100 μL) were suspended in dimethylformamide (DMF), to create a solution of 1.333 mg/mL polystyrene and 0.106 mg/mL anti-s100β in DMF. A piezoelectrically actuated pipette system (BioFluidix) was used to deposit 5.0 nL of this solution onto each sensor, as shown in FIG. 3. A close up view of a sensor after the solution was deposited is shown in FIG. 2.

The DMF was subsequently allowed to evaporate over a period of approximately 3 h. This resulted in functionalized sensors with a polystyrene/anti-s100β coating that allowed for the adsorption of s100β. Polystyrene was chosen as a coating due to its relatively low damping on the frequency response of the resonators as compared to other polymers. Anti-s100β was chosen to functionalize the sensors because of its high degree of specificity and affinity for s100β. DMF was chosen as the solvent because of its high evaporation rate and its ability to dissolve polystyrene without denaturing anti-s100β.

Confocal imaging was performed to confirm that the surface of the functionalized sensors would promote the adsorption of s100β. A functionalized sensor was exposed via micropipette to a solution of phosphate buffered saline (PBS) (Abcam) and a fluorescent conjugation of s100β containing a dye known as Alexa Fluor (Abcam, 100 μL). The exposed resonator was subsequently imaged with a confocal microscope to confirm the success of the functionalization. A 20× air lens was used with a pinhole size of 18.01 AU, a laser intensity of 2%, a gain of 750, and a 1.58 μs pixel dwell time. The fluorescent images taken confirmed the adsorption of the Alexa Fluor onto the surface of the resonator, validating the functionalization technique.

Forty seven sensors were functionalized as described. After functionalization, the frequency response of each sensor was obtained using the aforementioned experimental setup. An experimental group of 28 sensors was then exposed to 5.0 nL of a 19.6 μg/mL solution of s100β (Abcam, 500 μg) in PBS deposited directly onto the surface of the sensor using the piezoelectrically actuated pipette system. A control group of 19 separate sensors was exposed to 5.0 nL of PBS in the same manner. All of the sensors were subsequently rinsed with 5.0 nL of deionized water deposited onto each resonator again using the piezoelectrically actuated pipette system. After drying over a period of approximately 3 h, the frequency response of each sensor was again obtained.

Figure 4:
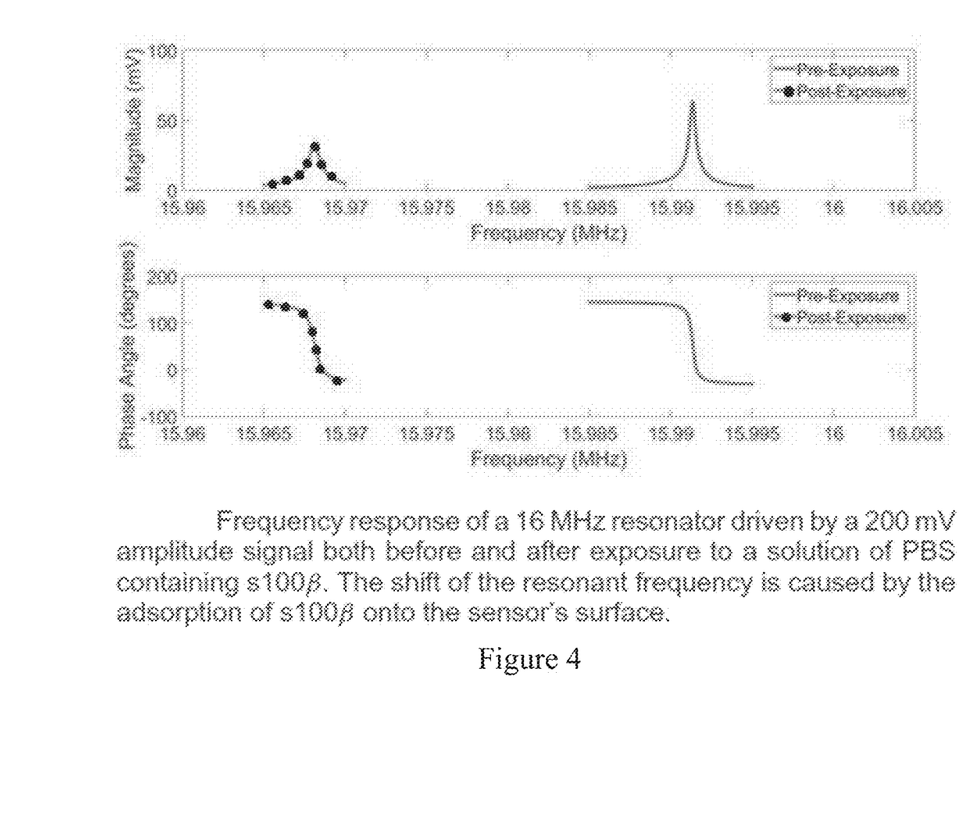
FIG. 4 illustrates a frequency response of a 16 MHz resonator driven by a 200 mV amplitude signal both before and after exposure to a solution of PBS containing s100β, in accordance with one or more embodiments.
Figure 5:
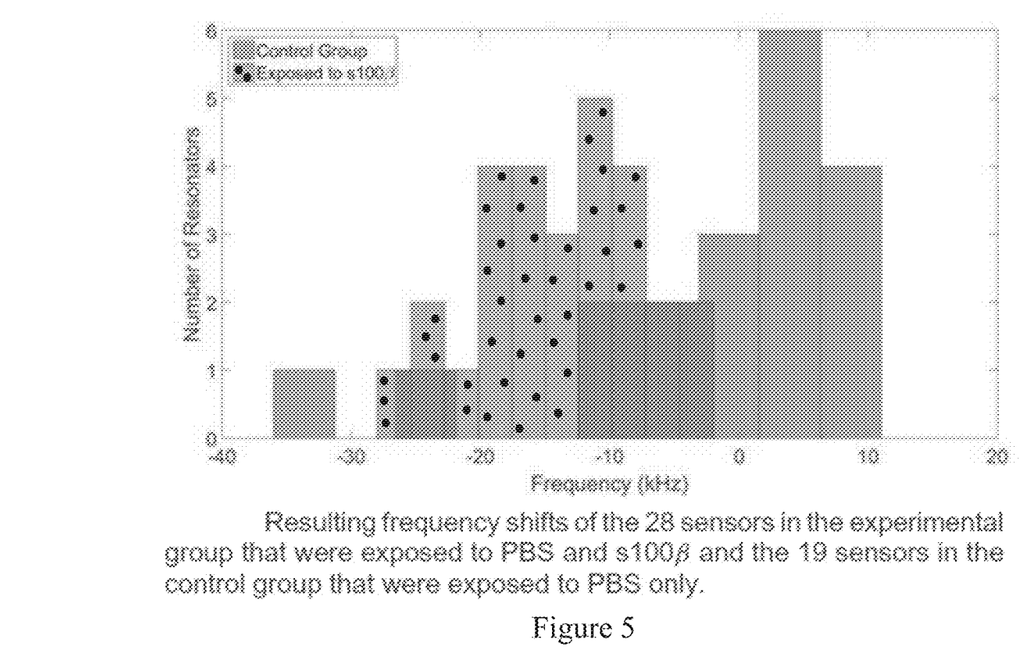
FIG. 5 illustrates frequency shifts of 28 resonators in an experimental group that were exposed to PBS and s100β and 19 sensors in the control group that were exposed to PBS only, in accordance with one or more embodiments.

Next, the relative shift in resonant frequency between the experimental group and the control group is calculated. An example of this shift is shown in FIG. 4. The resonant frequency shift of the sensor represented in FIG. 4 after exposure to s100β was 23244 Hz. The resonant frequency shifts of all of the sensors tested are presented in FIG. 5. The average frequency shift among the 28 resonators in the experimental group was 13704 Hz with a standard deviation of 6259 Hz. The average frequency shift among the 19 resonators in the control group was 1504 Hz with a standard deviation of 11431 Hz. Therefore, the average difference in the frequency shift between the experimental and control groups was 12200 Hz.

A one-sided, two-sample t-test was performed challenging the null hypothesis that the frequency shift experienced by the experimental group is equal to the frequency shift of the control group. The alternative hypothesis states that the average frequency shift experienced by the sensors in the experimental group is greater than the average frequency shift of the sensors in the control group. A small significance level of α=0.001 was chosen in order to minimize the risk of a Type I error. The resulting probability value was p=0.000012. Therefore, the null hypothesis was rejected, and the experiment provides strong statistical evidence of the successful detection of s100β.

The total amount of s100β deposited onto the sensors in the experimental group, determined by multiplying the concentration of s100β in the exposure solution by the volume deposited, was approximately 98 pg. This corresponds to an overall sensor sensitivity of 124.49 Hz/pg. This is theoretically sufficient to enable the detection of s100β in victims of TBI, who typically have s100β concentrations on the order of hundreds of ng/ml in their cerebrospinal fluid.

The invention is inclusive of combinations of the aspects described herein. References to "a particular aspect" and the like refer to features that are present in at least one aspect of the invention. Separate references to "an aspect" (or "embodiment") or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A method of detecting a substance, wherein the method comprises:
   functionalizing a plurality of sensors, wherein the functionalizing the plurality of sensors comprises depositing a first material using a piezoelectrically actuated pipette system, wherein the first material comprises a polymer, a receptor, and a solvent, wherein the solvent comprises dimethylformamide;
   evaporating a solution from the first material, wherein a residue after the evaporation comprises a functionalized chemical;
   introducing a control material to a first set of sensors of the plurality of sensors using the piezoelectrically actuated pipette system;
   introducing a test material to a second set of sensors of the plurality of sensors using the piezoelectrically actuated pipette system, wherein the test material comprises an analyte; and
   determining a difference between a first resonant frequency shift in the first set of sensors of the plurality of sensors and a second resonant frequency shift in the second set of sensors of the plurality of sensors.

2. The method of claim 1, wherein the polymer comprises polystyrene and the receptor comprises anti-s100β.

3. The method of claim 2, wherein the depositing the first material comprises depositing an amount of the suspension of polystyrene and anti-s100β in dimethylformamide on each sensor of the plurality of sensors, wherein the amount ranges from approximately $10^{-12}$ liters to approximately 10 milliliters.

4. The method of claim 3, wherein a concentration of polystyrene ranges from approximately 0.01 milligrams per milliliter to approximately 10 milligrams per milliliter, and a concentration of anti-s100β ranges from 0.01 milligrams per milliliter to approximately 10 milligrams per milliliter.

5. The method of claim 1, wherein the solution of the first material comprises dimethylformamide.

6. The method of claim 1, wherein the residue comprises a coating, wherein the coating comprises polystyrene and anti-s100β.

7. The method of claim 1, wherein the control material comprises phosphate buffered saline or water.

8. The method of claim 1, wherein the introducing the control material comprises introducing an amount of the control material to each sensor of the first set of sensors of the plurality of sensors, wherein the amount ranges from approximately $10^{-12}$ liters to approximately 10 milliliters.

9. The method of claim 1, wherein the analyte comprises s100β.

10. The method of claim 1, wherein the introducing the test material comprises introducing an amount of the test material to each sensor of the second set of sensors of the plurality of sensors, wherein the amount ranges from approximately $10^{-12}$ liters to approximately 10 milliliters.

11. The method of claim 9, wherein a concentration of s100β ranges from approximately $10^{-12}$ grams per milliliter to approximately 10 milligrams per milliliter.

12. The method of claim 1, wherein the determining the resonant frequency shift comprises using a lock-in amplifier.

13. The method of claim 1, wherein each sensor of the plurality of sensors is a quartz crystal resonator.

14. The method of claim 1, wherein each sensor of the plurality of sensors has a dimension of 3.2 mm by 2.5 mm.

15. The method of claim 2, wherein the depositing the first material comprises depositing an amount of the suspension of polystyrene and anti-s100β in dimethylformamide on each sensor of the plurality of sensors, wherein the amount is approximately 5 nano-liters.

16. The method of claim 3, wherein a concentration of polystyrene is approximately 1.333 mg/mL and a concentration of anti-s100β is approximately 0.106 mg/mL.

17. The method of claim 1, wherein the introducing the control material comprises introducing 5.0 nL of the control material to each sensor of the first set of sensors of the plurality of sensors.

18. The method of claim 9, wherein a concentration of s100β is 19.6 μg/mL.

19. The method of claim 1, wherein the introducing the test material comprises introducing 5.0 nL of the test material to each sensor of the second set of sensors of the plurality of sensors.

20. The method of claim 1, wherein the polymer comprises polycarbonate, Poly(methyl methacrylate), Acrylonitrile butadiene styrene, a synthetic polymer, Polybenzimidazole, Polycarbonate, Polyether sulfone, polyoxymethylene, polyetherether ketone, polyetherimide, polyethylene, polypropylene, or Poly(lactic acid).

* * * * *